(12) United States Patent
Mensitieri et al.

(10) Patent No.: US 7,071,327 B2
(45) Date of Patent: Jul. 4, 2006

(54) POLYSACCHARIDE-BASED SUPERABSORBENT FILM

(75) Inventors: Guiseppe Mensitieri, Naples (IT); Fabrizio Porro, Portici (IT); Luigi Nicolais, Ercolano (IT); Alessandro Sannino, Portici (IT)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/221,739

(22) PCT Filed: Mar. 9, 2001

(86) PCT No.: PCT/EP01/03863

§ 371 (c)(1),
(2), (4) Date: Dec. 27, 2002

(87) PCT Pub. No.: WO01/68713

PCT Pub. Date: Sep. 20, 2001

(65) Prior Publication Data

US 2003/0149263 A1 Aug. 7, 2003

(30) Foreign Application Priority Data

Mar. 16, 2000 (EP) ................................. 00200965

(51) Int. Cl.
*C07H 15/04* (2006.01)
*A61F 13/20* (2006.01)

(52) U.S. Cl. ......................... 536/120; 536/105; 536/56; 536/106; 536/114; 536/119; 536/123.1; 536/126; 536/118; 524/557; 604/374; 568/29

(58) Field of Classification Search ................ 536/105, 536/56, 106, 114, 119, 123.1, 124, 118, 120; 524/557; 568/29; 604/374

See application file for complete search history.

(56) References Cited

U.S. PATENT DOCUMENTS 5,414,135 A * 5/1995 Snow et al. .................. 568/29
6,143,821 A 11/2000 Houben

FOREIGN PATENT DOCUMENTS

| WO | WO 95/31500 | * 11/1995 |
| WO | WO9531500 | * 11/1995 |
| WO | 97/18890 | 5/1997 |
| WO | WO 97/18890 | * 5/1997 |

* cited by examiner

*Primary Examiner*—Shaojia A. Jiang
*Assistant Examiner*—Devesh Khare
(74) *Attorney, Agent, or Firm*—Buchanan Ingersoll PC

(57) ABSTRACT

A superabsorbent polysaccharide can be obtained by crosslinking a polysaccharide or derivative thereof with at least 1% by weight of a flexible spacer having a chain length of at least 9 chain atoms and having terminal activated coupling groups. The flexible spacer may comprise a polyalkyleneglycol with a molecular weight from about 400 to 10,000. The coupling groups may be provided by divinyl sulphone units.

20 Claims, No Drawings

POLYSACCHARIDE-BASED SUPERABSORBENT FILM

FIELD OF THE INVENTION

The present invention relates to flexible superabsorbent films based on polysaccharides such as cellulose and derivatives thereof, and to a process for producing such films.

BACKGROUND

Superabsorbent materials for use in hygiene products, which arc based on polysaccharides such as cellulose and starch, have recently become widely known in the art, for example in WO 98/27117. The absorbing capacity of such materials can be increased by crosslinking the polymers, e.g. by using epichlorohydrin, diglycidyl ethers, divinyl sulphone or other commonly known crosslinkers capable of reacting with hydroxyl groups, or by using carboxylated polysaccharides and crosslinkers capable of reacting with carboxyl groups, such as divalent metals. However, there is a demand for thinner absorbent products, which implies that superabsorbent materials have to be found which have further increased absorbing capacity and have increased flexibility.

WO 97/19116 describes superabsorbent acrylic polymers which are crosslinlked by polymerisation of acrylic acid in the presence of a combination of trimethylolpropane triacrylate or triallylamine, polyethyleneglycol mono(meth)acrylate monoallyl ether and polyethyleneglycol mono(meth)acrylate monoalkyl ether.

WO 97/31971 discloses similar, foamed superabsorbent acrylic polymers which are crosslinked e.g. with trimethytolpropane triacrylate, to which internal or external plasticisers (e.g. glycerol or acrylic esters) may added to increase flexibility of the foam.

DESCRIPTION OF THE INVENTION

It has been found that thin superabsorbent polysaccharides with high absorption capacity and sufficient flexibility can be obtained by crosslinking the polysaccharides with flexible spacers such as polyalkyleneglycols, having terminal activated groups. The products and the process of producing them are defined in the appending claims.

The polysaccharides to be used according to the present invention are in particular α-glucans like starch, amylose and amylopectin, β-glucans like cellulose, galactomannans like guar gum (guaran) and locust bean gum, glucomannans including e.g. xanthan gum, fructans, (arabino)xylans and galactans, as well as derivatives such as carboxymethyl, alkyl, hydroxyethyl and hydroxypropyl derivatives of such polysaccharides. Cellulose and cellulose derivatives are preferred for practical reasons. Combinations of such polysaccharides, or combinations with other polymers such as polyacrylates, polyvinyl alcohol etc. can also be used. The chain length of the polysaccharides is important, although there is no critical minimum for the molecular weight. In general, polysaccharides having a molecular weight of more than 25,000 are preferred.

The polysaccharides to be used according to the present invention may also be carboxymethylated or carboxyethylated, especially in the case of cellulose. Other carboxyalkylated polysaccharides include the half esters obtained from cyclic anhydrides such as succinic and maleic anhydride, and addition products of maleic half esters to which sulphite has been added. The degree of carboxyalkylation is preferably between 0 and 1.5, in particular between 0.1 and 1.0 carboxyalkyl groups per monosaccharide unit. The carboxyl derivatives may be in their acid or in salt form. Combinations of carboxylated polysaccharides such as CMC (carboxymethyl cellulose) and hydroxyallylated polysacharides (e.g. hydroxyethyl cellulose, HEC) are especially useful, whether as mixtures of different derivatives (e.g. HEC and CMC, or HEC and carboxymethyl starch, or HEC and methyl cellulose) or as multiply derivatised single compounds (e.g. sodium carboxymethyl-hydroxyethyl cellulose, CMHEC)

The polyalkyleneglycols to be used as spacers may for example be polyethyleneglycol (PEG), polypropyleneglycol (PPG) and the like. Other hydrophilic or hydrophobic spacers may also be used, as long as they are flexible, i.e. contain no or only a few double bonds or cyclic structures; examples are polyalkylene (as in decamethylene diisocyanate), polyhydroxyalkylene, polyalkylene succinate, polylactide, etc, with chain lengths from about 9 to about 750 chain atoms. The chain length of the polyalkyleneglycols may vary from edgy 3 units (MW about 150 Da) up to e.g. 250 (MW about 11,000). Molecular weights from about 1000 to about 8000 are preferred. The relative amount of polyalkyleneglycol with respect to the polysaccharide may vary from about 1/200 to about 1/1, especially from about 1/50 to about 1/1.5 (weight ratios), depending on the required thickness and the required flexibility of the product.

The terminal activated groups are preferably vinyl groups activated by carbonyl or sulphonyl functions, for example acryloyl groups ($-CO-CR=CHR$), maleoyl groups ($-CO-CH=CH-COOH$) or vinylsulphonyl groups ($-SO_2-CR=CHR$), in which each R may be hydrogen (preferred), methyl or other alkyl. Such groups may be directly attached to the polyalkyleneglycol, e.g. as (sulphonate) esters, or through alkylene or phenylene groups. Particularly advantageous is the coupling product of a polyalkyleneglycol with divinyl sulphone on either side of the polyglycol. Other terminal crosslinkers include (activated) halomethyl, activated hydroxymethyl, activated formyl, epoxy, isocyanate, and the like. Examples of such coupling agents (other than divinyl sulphone) are maleic anhydride, dichloroacetone, 1,3-dichloro-2-propanol, dimethylourea, dimethylolimidazolidone, diepoxides such as bisepoxybutane or bis(glycidyl ether), epichlorohydrin, diisocyanates, bis(2-hydroxyethyl) sulphone, formaldehyde, glyoxal. The weight ratio between terminal crosslinker (such as divinyl sulphone) and spacer (such as polyalkylene glycol) can be between about 1/1 to about 100/1, especially between about 1.5/1 and 30/1. The weight ratio between crosslinker and polysaccharide may vary from e.g. 1/1 to 1/50, especially form 1/1.5 to 1/10.

The production of the superabsorbent films according to the invention can be divided in three steps: (1) mixing of reactants and other compounds, (2) reaction and washing stage, and (3) desiccation. As to step (1), the components involved in the reaction can be divided in different classes: (a) components of the base structure of the network, i.e. the polysaccharides, e.g. carboxymethyl cellulose sodium salt (CMCNa) and/or hydroxyethyl cellulose (HEC); (b) crosslinkers, e.g. divinyl sulphone (DVS); (c) spacers, e.g. polyethylene glycol (PEG); (d) catalysts, e.g. KOH; and solvents, e.g. water. In step (2), the reactants are allowed to react for a sufficient time to allow the production of a crosslinked gel. Preferably, the polyalkylene glycol and the reagent introducing the terminal double bonds are reacted first, followed by reaction with the polysaccharide, preferably in the presence of an alkaline catalyst. The crosslinking reaction can be performed at varying temperatures e.g. from about 5° C. to about 40° C., for about 1 hour to about 2 days, preferably form 5–24 hours. After the crosslinking, the unreacted reagents can be removed by washing in distilled water, if desired, followed by drying. The crosslinked product can also be directly dried without a washing step.

The superabsorbent products according to the invention are flexible films with thicknesses between 10 and 500 μm and having absorption capacities between about 15 and 30 g of synthetic urine (300 mM urea, 60 mM KCl, 130 mM NaCl, 2.0 mM $CaSO_4$, 3.5 mM $MgSO_4$, 29 MM $KH_2PO_4$, 5.3 MM $Na_2HPO_4$, 1 mg/l Triton X-100 in deionised water) per g of product. They can be used in absorbent articles, such as diapers, incontinence guards, sanitary napkins, and the like. They can also be used in tissue papers including kitchen towels, napkins, industrial wipes and the like.

EXAMPLES

Materials: Divinyl sulphone (DVS), polyethyleneglycol (PEG) with various molecular weights (400, 4600, 10,000), hydroxyethyl cellulose (HEC, MW 250,000) and carboxymethyl cellulose (CMCNa, MW 700,000) were obtained from Aldrich Chimica, Milano, IT.

The amounts of reagents are given in the tables, per 150 ml of distilled water. DVS was dissolved in distilled water to a concentration of 40 mmol/l. PEG was then added to the DVS solution. After dissolution of the PEG the CM CNa and HEC were added in powder form and dissolved up to a concentration of about 2% (see tables). Best results were obtained by first dissolving HEC and then slowly admixing CMCNa. Mixing was continued at 25° C. until a clear solution was obtained. After complete mixing, 1M of aqueous KOH was dissolved into the mixture up to the desired concentration. After another two minutes of stirring the reaction mixture was spread on a teflon sheet with a Gardner knife in order to obtain a film with a controlled thickness. The film was allowed to crosslink at ambient temperature for between 5 and 24 hours (best results after 10–14 hours). Higher temperatures did not increase the crosslinking rate, and resulted in decreased viscosity. A thin, partially swollen gel film was obtained.

From this point on, two different procedures were followed. According to the first procedure, the teflon sheet with the partly swollen film was then put in a jar containing distilled water. As soon as the film started to swell further, the teflon sheet was removed. During swelling, water mixture containing residual KOH, unreacted DVS and other impurities was continuously removed from the bottom of the jar, while fresh distilled water was added. After equilibrium swelling occurred, the teflon sheet was again positioned under the film, water around the film was removed and the film was dried under atmospheric conditions.

According to the second procedure, the washing (addition and removal of water) was omitted and the swelling film was maintained on the teflon sheet for 5–24 hours and then dried under atmospheric conditions.

As an alternative to drying under atmospheric conditions (for about 6–20 days), desiccation was performed in an oven at 50–100° C., with best results being obtained at 60–80° C., for 1–24 hours.

TABLE 1

Hydrogel synthesis mixture with PEG 400
Molar ratio [PEG]/[DVS] = 1/30; molar ratio [PEG]/[cellulose] = 16/1

| Reagent | grams | mmoles | % by weight |
|---|---|---|---|
| Water | 150 | 8330 + 280[1] | 94.54 |
| CMCNa | 2.25 | 3.21 * $10^{-3}$ | 1.42 |
| HEC | 0.75 | 3.00 * $10^{-3}$ | 0.47 |
| KOH, 1 M in water | 5.28 | KOH: 5.00 | 3.33 |
| DVS | 0.35 | 2.96 | 0.22 |
| PEG 400 | 0.04 | 0.100 | 0.03 |

[1]the water of the KOH solution

TABLE 2

Hydrogel synthesis mixture with PEG 400
Molar ratio [PEG]/[DVS] = 1/90; molar ratio [PEG]/[cellulose] = 11/1

| Reagent | grams | mmoles | % by weight |
|---|---|---|---|
| Water | 150 | 8330 + 280[1] | 94.33 |
| CMCNa | 2.25 | 3.21 * $10^{-3}$ | 1.41 |
| HEC | 0.75 | 3.00 * $10^{-3}$ | 0.47 |
| KOH, 1 M in water | 5.28 | KOH: 5.00 | 3.32 |
| DVS | 0.71 | 6.01 | 0.45 |
| PEG 400 | 0.027 | 0.0675 | 0.02 |

[1]the water of the KOH solution

TABLE 3

Hydrogel synthesis mixture with PEG 400
Molar ratio [PEG]/[DVS] = 1/60; molar ratio [PEG]/[cellulose] = 16/1

| Reagent | grams | mmoles | % by weight |
|---|---|---|---|
| Water | 150 | 8330 + 280[1] | 94.32 |
| CMCNa | 2.25 | 3.21 * $10^{-3}$ | 1.41 |
| HEC | 0.75 | 3.00 * $10^{-3}$ | 0.47 |
| KOH, 1 M in water | 5.28 | KOH: 5.00 | 3.32 |
| DVS | 0.71 | 6.01 | 0.45 |
| PEG 400 | 0.04 | 0.100 | 0.03 |

[1]the water of the KOH solution

TABLE 4

Hydrogel synthesis mixture with PEG 400
Molar ratio [PEG]/[DVS] = 1/10; molar ratio [PEG]/[cellulose] = 96/1

| Reagent | grams | mmoles | % by weight |
|---|---|---|---|
| Water | 150 | 8330 + 280[1] | 94.20 |
| CMCNa | 2.25 | 3.21 * $10^{-3}$ | 1.41 |
| HEC | 0.75 | 3.00 * $10^{-3}$ | 0.47 |
| KOH, 1 M in water | 5.28 | KOH: 5.00 | 3.32 |
| DVS | 0.71 | 6.01 | 0.45 |
| PEG 400 | 0.24 | 0.600 | 0.15 |

[1]the water of the KOH solution

TABLE 5

Hydrogel synthesis mixture with PEG 400
Molar ratio [PEG]/[DVS] = 1/200; molar ratio [PEG]/[cellulose] = 16/1

| Reagent | grams | mmoles | % by weight |
|---|---|---|---|
| Water | 150 | 8330 + 280[1] | 93.36 |
| CMCNa | 2.25 | 3.21 * $10^{-3}$ | 1.40 |
| HEC | 0.75 | 3.00 * $10^{-3}$ | 0.47 |
| KOH, 1 M in water | 5.28 | KOH: 5.00 | 3.29 |

TABLE 5-continued

Hydrogel synthesis mixture with PEG 400
Molar ratio [PEG]/[DVS] = 1/200; molar ratio [PEG]/[cellulose] = 16/1

| Reagent | grams | mmoles | % by weight |
|---------|-------|--------|-------------|
| DVS     | 2.35  | 19.9   | 1.46        |
| PEG 400 | 0.04  | 0.100  | 0.03        |

[1] the water of the KOH solution

TABLE 6

Hydrogel synthesis mixture with PEG 400
Molar ratio [PEG]/[DVS] = 1/100; molar ratio [PEG]/[cellulose] = 32/1

| Reagent        | grams | mmoles          | % by weight |
|----------------|-------|-----------------|-------------|
| Water          | 150   | 8330 + 280[1]   | 93.34       |
| CMCNa          | 2.25  | $3.21 * 10^{-3}$ | 1.40       |
| HEC            | 0.75  | $3.00 * 10^{-3}$ | 0.47       |
| KOH, 1 M in water | 5.28 | KOH: 5.00      | 3.29        |
| DVS            | 2.35  | 19.9            | 1.46        |
| PEG 400        | 0.08  | 0.200           | 0.05        |

[1] the water of the KOH solution

TABLE 7

Hydrogel synthesis mixture with PEG 4600
Molar ratio [PEG]/[DVS] = 1/30; molar ratio [PEG]/[cellulose] = 16/1

| Reagent        | grams | mmoles          | % by weight |
|----------------|-------|-----------------|-------------|
| Water          | 150   | 8330 + 280[1]   | 94.29       |
| CMCNa          | 2.25  | $3.21 * 10^{-3}$ | 1.41       |
| HEC            | 0.75  | $3.00 * 10^{-3}$ | 0.47       |
| KOH, 1 M in water | 5.28 | KOH: 5.00      | 3.32        |
| DVS            | 0.35  | 2.96            | 0.22        |
| PEG 400        | 0.46  | 0.100           | 0.29        |

[1] the water of the KOH solution

TABLE 8

Hydrogel synthesis mixture with PEG 4600
Molar ratio [PEG]/[DVS] = 1/60; molar ratio [PEG]/[cellulose] = 16/1

| Reagent        | grams | mmoles          | % by weight |
|----------------|-------|-----------------|-------------|
| Water          | 150   | 8330 + 280[1]   | 94.07       |
| CMCNa          | 2.25  | $3.21 * 10^{-3}$ | 1.41       |
| HEC            | 0.75  | $3.00 * 10^{-3}$ | 0.47       |
| KOH, 1 M in water | 5.28 | KOH: 5.00      | 3.31        |
| DVS            | 0.71  | 6.01            | 0.45        |
| PEG 400        | 0.46  | 0.100           | 0.29        |

[1] the water of the KOH solution

TABLE 9

Hydrogel synthesis mixture with PEG 4600
Molar ratio [PEG]/[DVS] = 1/33; molar ratio [PEG]/[cellulose] = 96/1

| Reagent        | grams | mmoles          | % by weight |
|----------------|-------|-----------------|-------------|
| Water          | 150   | 8330 + 280[1]   | 91.80       |
| CMCNa          | 2.25  | $3.21 * 10^{-3}$ | 1.38       |
| HEC            | 0.75  | $3.00 * 10^{-3}$ | 0.46       |
| KOH, 1 M in water | 5.28 | KOH: 5.00      | 3.23        |

TABLE 9-continued

Hydrogel synthesis mixture with PEG 4600
Molar ratio [PEG]/[DVS] = 1/33; molar ratio [PEG]/[cellulose] = 96/1

| Reagent | grams | mmoles | % by weight |
|---------|-------|--------|-------------|
| DVS     | 2.35  | 19.9   | 1.44        |
| PEG 400 | 2.76  | 0.600  | 1.69        |

[1] the water of the KOH solution

TABLE 10

Hydrogel synthesis mixture with PEG 10,000
Molar ratio [PEG]/[DVS] = 1/30; molar ratio [PEG]/[cellulose] = 16/1

| Reagent        | grams | mmoles          | % by weight |
|----------------|-------|-----------------|-------------|
| Water          | 150   | 8330 + 280[1]   | 93.97       |
| CMCNa          | 2.25  | $3.21 * 10^{-3}$ | 1.41       |
| HEC            | 0.75  | $3.00 * 10^{-3}$ | 0.47       |
| KOH, 1 M in water | 5.28 | KOH: 5.00      | 3.31        |
| DVS            | 0.35  | 2.96            | 0.22        |
| PEG 400        | 1.00  | 0.100           | 0.63        |

[1] the water of the KOH solution

The invention claimed is:

1. A process for producing a crosslinked flexible superabsorbent polysaccharide, comprising reacting a polyalkyleneglycol with at least two equivalents of a reagent containing one or more activated double bonds selected from the group consisting of divinyl sulphone, maleic anhydride, dichloroacetone, 1,3-dichloro-2-propanol, dimethylolurea, dimethylolimidazolidone, diexpoides, epichlorohydrin, diisocyanates, bis(2-hydroxyethyl) sulphone, formaldehyde, and glyoxal, to form a crosslinking spacer having a chain length of at least 9 chain atoms and having terminal activated coupling groups and reacting at least 1% by weight of the crosslinking spacer with a polysaccharide or a derivative thereof selected from the group consisting of carboxymethyl, alkyl, hydroxyethyl and hydroxypropyl derivatives in the presence of a catalyst.

2. A hygiene product containing a crosslinked flexible superabsorbent polysaccharide film produced according to the process of claim 1.

3. The process according to claim 1, wherein said reagent comprises divinyl sulphone.

4. A crosslinked flexible superabsorbent polysaccharide produced by the process claim 1.

5. The crosslinked flexible superabsorbent polysacoharide according to claim 4, wherein said polysaccharide has a molecular weight, before crosslinking, of between 250,000 and 1,000,000 kD.

6. The crosslinked flexible superabsorbent polysaccharide according to claim 4, in which said polyalkyleneglycol has a molecular weight from about 400 to 10,000 kD.

7. The crosslinked flexible superabsorbent polysaccharide according to claim 4, in which said polyalkyleneglycol is polyethyleneglycol.

8. The crosslinked flexible superabsorbent polysaccharide according to claim 4, in which said coupling groups comprise vinyl sulphone groups.

9. The crosslinked flexible superabsorbent polysaccharide according to claim 4, in which 10–67% by weight of the crosslinking spacer, with respect to the polysaccharide, has been used.

10. The crosslinked flexible superabsorbent polysaccharide according to claim 4, in which said polysaccharide has a molecular weight, before crosslinking, of between 100,000 and 1,500,000 kD.

11. The crosslinked flexible superabsorbent polysaccharide according to claim 4, which has the form of a film having a thickness of between 10 and 500 µm.

12. A hygiene product containing a crosslinked flexible superabsorbent polysaceharide film according to claim 11.

13. A process for producing a crosslinked flexible superabsorbent polysaccharide comprising reacting a spacer selected from the group consisting of polyalkyleneglycol, polyalkylene, decamethylene diisocyanate, polyhydroxyalkylene, polyalkylene succinate, and polylactide with at least two equivalents of a reagent containing one or more activated double bonds to form a crosslinking spacer having a chain length of at least 9 chain atoms and having terminal activated coupling groups selected from the group consisting of acrylol groups, maleoyl groups, and vinylsulphonyl groups and reacting at least 1% by weight of the crosslinking spacer with a polysaccharide or a derivative thereof selected from the group consisting of carboxymethyl, alkyl, hydroxyethyl and hydroxypropyl derivatives in the presence of a catalyst.

14. A crosslinked flexible superabsorbent polysaccharide produced by the process of claim 13.

15. The crosslinked flexible superabsorbent polysaccharide according to claim 14, in which said activated coupling groups are selected from the group consisting of acrylol groups, maleoyl groups, and vinylsulphonyl groups.

16. The crosslinked flexible superabsorbent polysaccharide according to claim 14, in which said coupling groups comprise vinyl sulphone groups.

17. The crosslinked flexible superabsorbent polysaccharide according to claim 14, in which 10–67% by weight of the crosslinking spacer, with respect to the polysaccharide, has been used.

18. The crosslinked flexible superabsorbent polysaccharide according to claim 14, in which said polysaccharide has a molecular weight, before crosslinking, of between 100,000 and 1,500,000 kD.

19. The crosslinked flexible superabsorbent polysaccharide according to claim 14, which has the form of a film having a thickness of between 10 and 500 µm.

20. A hygiene product containing a crosslinked flexible superabsorbent polysacoharide film according to claim 19.

* * * * *